(12) United States Patent
Chen et al.

(10) Patent No.: US 8,062,593 B2
(45) Date of Patent: Nov. 22, 2011

(54) CELL/TISSUE MASS SELECTING APPARATUS AND DIVIDING MECHANISM THEREOF

(75) Inventors: Wannhsin Chen, Hsinchu (TW);
Lih-Tao Hsu, Taoyuan County (TW);
Yeou-Bin Guu, Taichung (TW); Yu Mei Chen, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 12/825,136

(22) Filed: Jun. 28, 2010

(65) Prior Publication Data
US 2010/0261261 A1   Oct. 14, 2010

Related U.S. Application Data

(62) Division of application No. 11/965,528, filed on Dec. 27, 2007, now Pat. No. 7,842,236.

(30) Foreign Application Priority Data

Dec. 20, 2007 (TW) ................................ 96148899 A

(51) Int. Cl.
*G01N 21/00* (2006.01)

(52) U.S. Cl. ................ 422/63; 422/64; 422/65; 422/66; 422/67; 83/169; 83/170

(58) Field of Classification Search .............. 422/65–67, 422/63, 64; 83/169–170
See application file for complete search history.

(56) References Cited

U.S. PATENT DOCUMENTS

| 4,393,588 A * | 7/1983 | Kowalski ...................... 30/196 |
| 4,971,067 A | 11/1990 | Bolduc et al. |
| 5,389,104 A | 2/1995 | Hahnen et al. |
| 2006/0141616 A1 | 6/2006 | Guu et al. |

FOREIGN PATENT DOCUMENTS

| JP | 5237120 | 9/1993 |
| TW | 200621197 | 7/2006 |

OTHER PUBLICATIONS

China Patent office, Office Action, Patent Application Serial No. 200710305455.4, Mar. 24, 2011, China.
Taiwan Patent Office, Office Action, Patent Application Serial No. 096148899, Apr. 14, 2011, Taiwan.
Great Britain Patent Office, Office Action, Patent Application No. 1005984.8, Jan. 20, 2011, Great Britain.

* cited by examiner

*Primary Examiner* — Jyoti Nagpaul

(57) ABSTRACT

A selecting apparatus for selecting cell/tissue mass includes a base, a feeding mechanism and a dividing mechanism. The base has a platform for placing the cell/tissue mass. The feeding mechanism, disposed on the base, moves relative to the platform. The dividing mechanism, disposed on the feeding mechanism, includes a first cutting set and a second cutting set connected therewith. The second cutting set reciprocally moves between a first position and a second position, toward the first cutting set. The feeding mechanism moves the dividing mechanism above the platform, aligning the dividing mechanism with a portion of the cell/tissue mass, and moves the first cutting set toward the cell/tissue mass, cutting into the portion of the cell/tissue mass. The second cutting set moves from the first position to the second position, limiting the portion of the cell/tissue mass between the first cutting set and the second cutting set.

9 Claims, 5 Drawing Sheets

CELL/TISSUE MASS SELECTING APPARATUS AND DIVIDING MECHANISM THEREOF

This application is a divisional of U.S. application Ser. No. 11/965,528, filed Dec. 27, 2007, the entire disclosure of which is hereby incorporated by reference.

BACKGROUND OF THE INVENTION

1. Field of the Invention

The invention relates to a cell/tissue mass selecting apparatus, and in particular, to a cell/tissue mass selecting apparatus utilizing a clamping-type dividing mechanism to complete multi procedures such as auto-selecting, cutting and transferring the cell/tissue mass.

2. Description of the Related Art

The cultivation of human embryonic stem is carried out by cultivating a cell mass on feeder cells or extracellular matrix. When proceeding in subculture, the cell mass is first divided into pieces, and then the selected piece is transferred to new feeder cells or extracellular matrix for further cultivation. However, the subculturing procedure is mostly accomplished by manual operation, resulting in inefficient use of time and increased possibility for cell differentiation and contamination.

A mechanical tool has been disclosed and is utilized for subculturing of cells, such as a cell subculturing device of Taiwan patent application No. 93141042. However, shortcomings are also noted. Cell mass is divided into pieces by a cutting mechanism, and a piece is then selected by a transferring mechanism. The transferring mechanism comprises a collecting stitch aligning with the selected piece and picking up the selected piece by suction.

The conventional cell subculturing device divides the cell in matrix and selects the divided piece from the cell mass. In other words, the cell subculturing device cannot select and cut an appointed area of the cell mass. Additionally, the cutting mechanism and the transferring mechanism have to work in cooperation to accomplish the subculture.

BRIEF SUMMARY OF THE INVENTION

The invention provides a cell/tissue mass selecting apparatus for selecting cell/tissue mass. The cell/tissue mass selecting apparatus comprises a base, a feeding mechanism and a dividing mechanism. The base has a platform for placing the cell/tissue mass. The feeding mechanism, disposed on the base, moves relative to the platform. The dividing mechanism, disposed on the feeding mechanism, comprises a first cutting set and a second cutting set connected therewith. The second cutting set reciprocally moves between a first position and a second position toward the first cutting set. The feeding mechanism moves the dividing mechanism above the platform, aligning the dividing mechanism with a portion of the cell/tissue mass, and moves the first cutting set toward the cell/tissue mass, cutting into the portion of the cell/tissue mass. The second cutting set moves from the first position to the second position, limiting the portion of the cell/tissue mass between the first cutting set and the second cutting set. The feeding mechanism moves the dividing mechanism to a predetermined position, and usually the position is set to align with a carrier substrate. The second cutting set moves from the second position to the first position in a direction opposite to the first cutting set, allowing the portion of the cell/tissue mass to separate from the first cutting set and the second cutting set. The portion of the cell/tissue mass is then separated therefrom and dropped to the carrier substrate. The procedure is completed automatically, providing rapid and precise passaging of the cell/tissue mass.

The invention provides a dividing mechanism for dividing cell/tissue mass. The dividing mechanism comprises a first cutting set and a second cutting set. The first cutting set comprises a first cutting member and a second cutting member in parallel with the first cutting member. The second cutting set, connected with the first cutting set, rotates toward a direction in parallel with the first cutting member and the second cutting member, wherein two sides of the second cutting set abut the first cutting member and the second cutting member, respectively.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1:
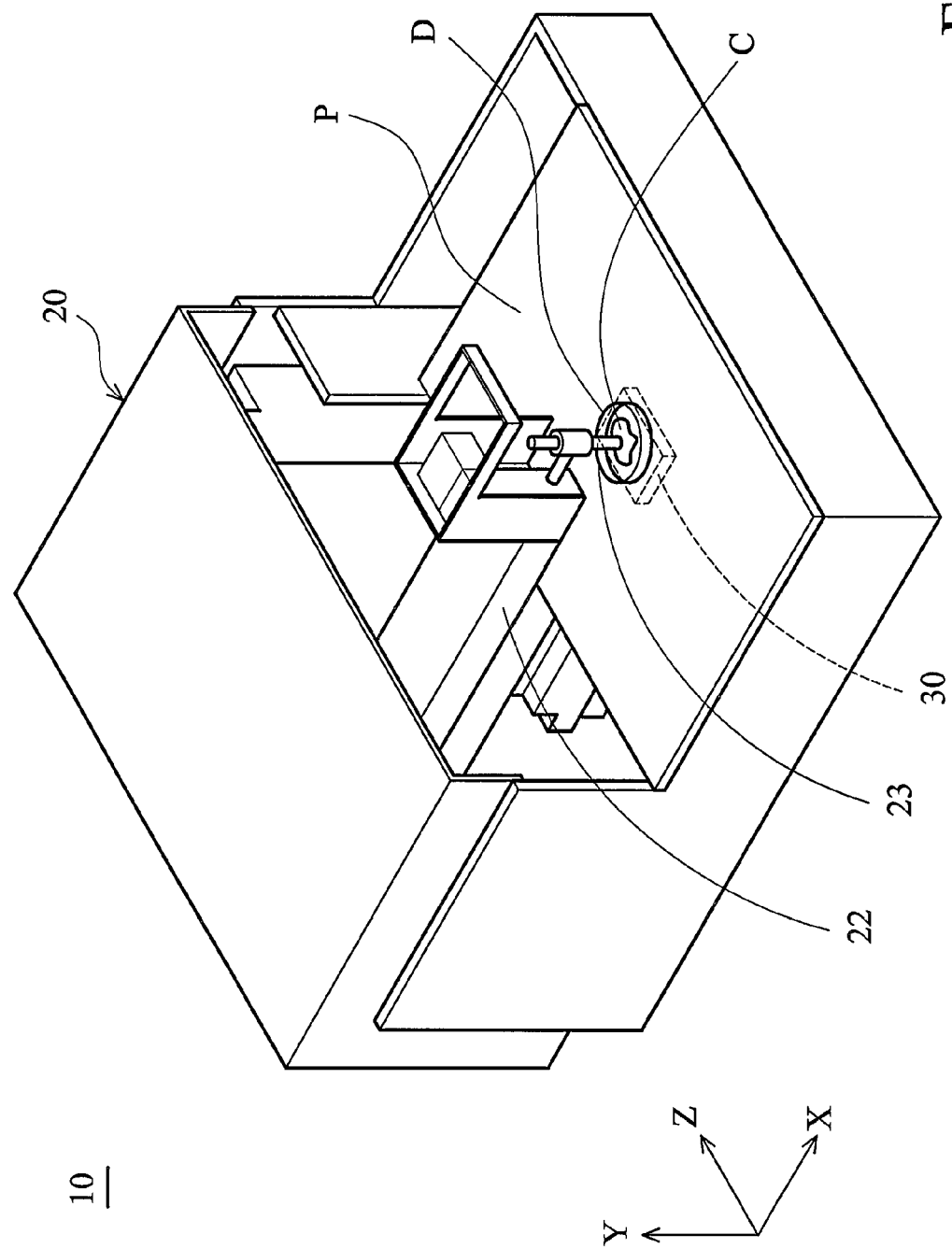
FIG. 1 is a schematic view of a selecting apparatus of the invention.
Figure 2A:
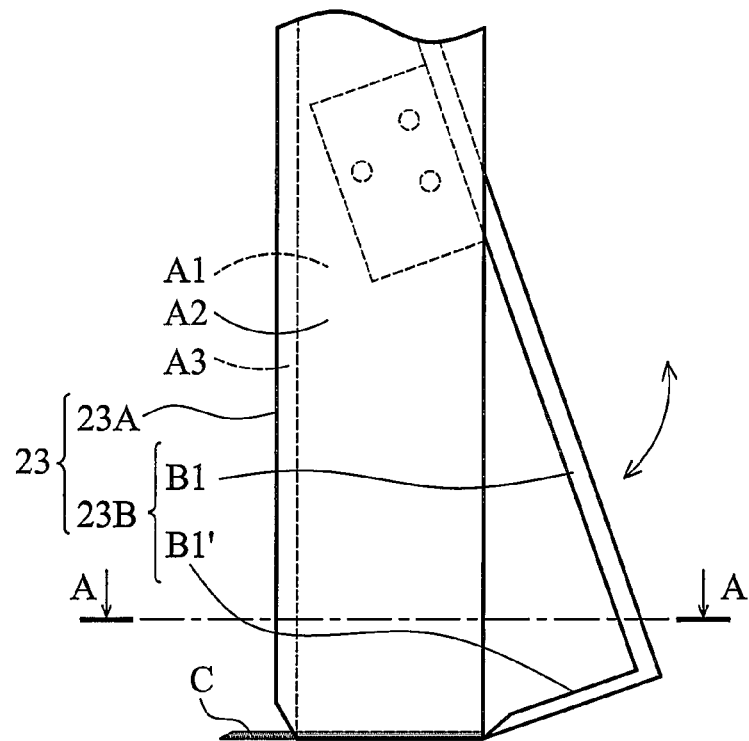
FIGS. 2A and 2B are schematic views of a dividing mechanism of the invention.
Figure 2B:
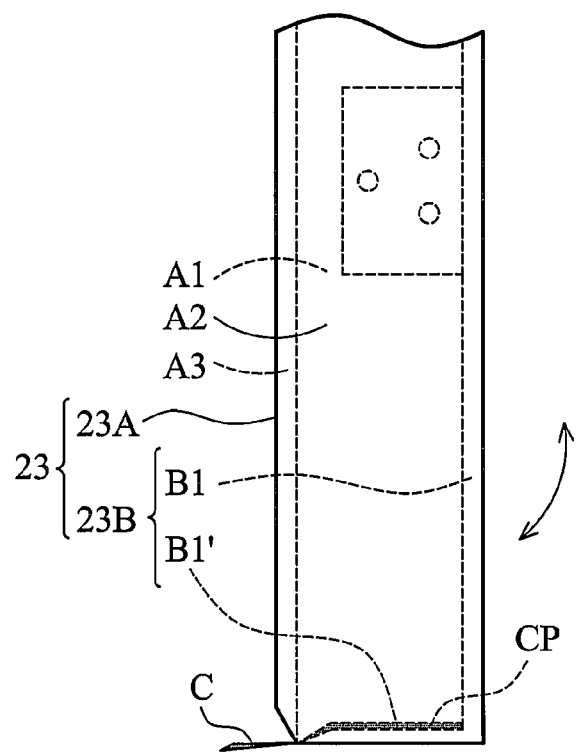

As shown in FIGS. 1, 2A and 2B, the invention provides a selecting mechanism 10 for selecting cell/tissue mass C, such as human embryonic stem cell colony. The selecting mechanism 10 comprises a base 20, a feeding mechanism 22, a dividing mechanism 2 for dividing the cell/tissue mass C, and an image capturing assembly 30.

The base 20 has a transparent platform P for placing a carrier D (Petri dish, glass slide and etc.) carried with the cell/tissue mass C. Human embryonic stem cell colony has a diameter about 1 mm to 3 mm. The image capturing assembly 30, disposed in the base 20 and below the platform P, captures the image of the cell/tissue mass C through the platform P. The feeding mechanism 22, disposed on the base 20, moves relative to the platform P in an X direction, a Y direction and a Z direction. The dividing mechanism 23 is disposed on the feeding mechanism 22. When the feeding mechanism 22 moves relative to the platform P, the dividing mechanism 23 is moved simultaneously.

After the image capturing assembly 30 captures the image of the cell/tissue mass C, the image is analyzed by a control unit to further control the movement of the feeding mechanism 22, aligning the dividing mechanism 23 with a portion CP, a desired cutting portion, of the cell/tissue mass C. For example, a piece of human embryonic stem cell is cut to be about 0.01 $mm^2$ to 1 $mm^2$.

The dividing mechanism 23 comprises a first cutting set 23A and a second cutting set 23B (as shown in FIGS. 2A and 2B). The second cutting set 23B is pivotally disposed on the first cutting set 23A, and a edge portion B1' of the second cutting set 23B reciprocally moves between a first position (as shown in FIG. 2A) and a second position (as shown in FIG.

2B), toward the first cutting set 23A, for cutting and clamping the portion CP of the cell/tissue mass C.

Figure 3A:
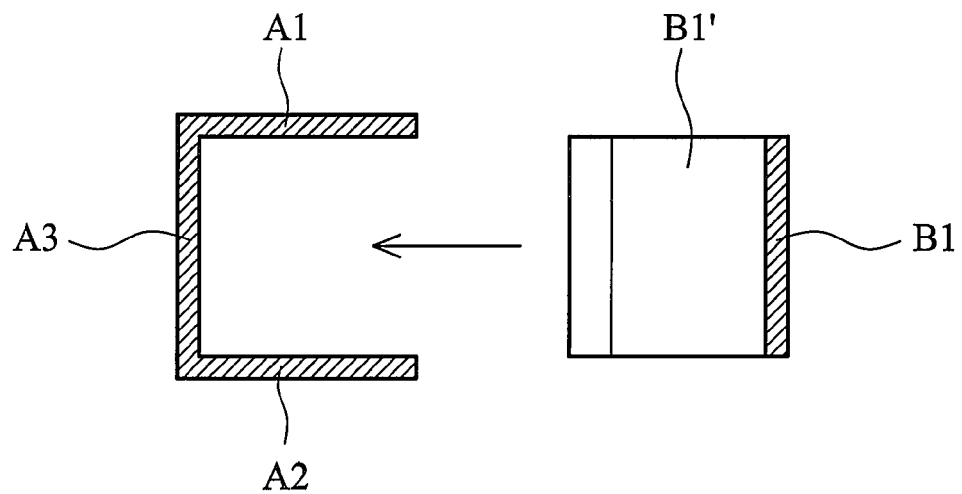
FIG. 3A is a sectional view along line A-A' in FIG. 2A.

Referring to FIGS. 2A, 2B and 3A at the same time, the first cutting set 23A comprises a first cutting member A1, a second cutting member A2 and a third cutting member A3, wherein the first cutting member A1 and the second cutting member A2 are in parallel to each other and connected to each other by the third cutting member A3. The second cutting set 23B comprises the blade portion B1 and an edge portion B1'. The edge portion B1' is perpendicular to the blade portion B1 and two sides of the edge portion B1' abut the first cutting member A1 and the second cutting member A2. Additionally, the edge portion B1' and the third cutting member A3 comprise the same or complementary shapes.

Figure 3B:
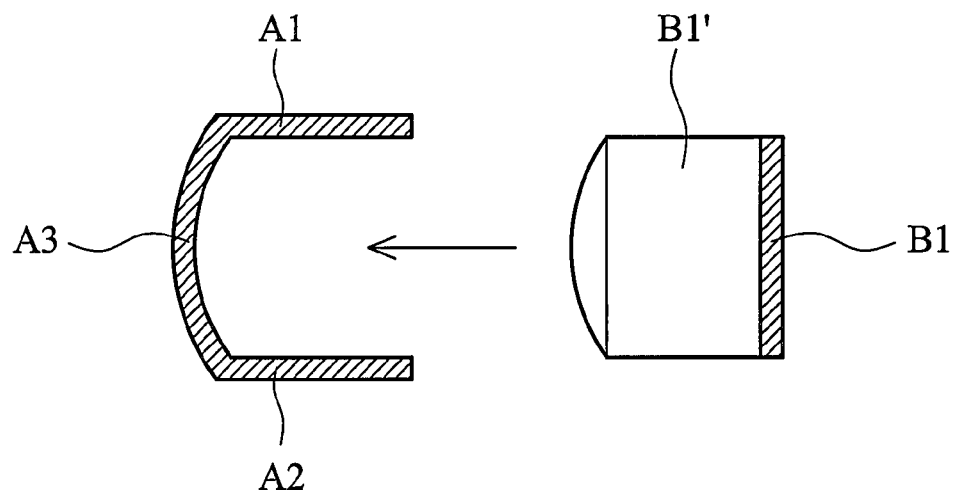
FIG. 3B is a sectional view of a variant embodiment of the dividing mechanism in FIG. 2A.

It should be noted that in the embodiment, the third cutting member A3 and the edge portion B1' of the second cutting set 23B comprise linear shapes, but it is not limited thereto. Referring to FIG. 3B, the third cutting member A3 and the edge portion B1' of the second cutting set 23B may comprise complementary curved shapes or other shapes.

Referring to FIGS. 2A and 2B again, after the dividing mechanism 23 aligns with the portion CP of the cell/tissue mass C, the feeding mechanism 22 moves in the Y direction toward the cell/tissue mass C, allowing the first cutting set 23A to cut into the portion CP. Next the second cutting set 23B rotates from the first position to the second position (as shown in FIG. 2B), allowing the edge portion B1' to cut into the cell/tissue mass C. The second cutting set 23B continuously moves to shovel the portion CP of the cell/tissue mass C, such that the portion CP can be separated from the cell/tissue mass C and be limited between the first cutting set 23A and the second cutting set 23B. Furthermore, because the two sides of the second cutting set 23B abut with the first cutting member A1 and the second cutting member A2, respectively, the portion CP of the cell/tissue mass C is completely shoveled by the second cutting set 23B during the rotation of the second cutting set 23B toward the first cutting set 23A (as shown in FIG. 2B).

Referring to FIGS. 4A, 4B, 5A and 5B, in another embodiment of the invention, the first cutting set 23A of the dividing mechanism 23' comprises a first cutting member A1 and a second cutting member A2, and the second cutting set 23B thereof comprises a fourth cutting member A4 and a fifth cutting member A5. The fourth cutting member A4 and the fifth cutting member A5, pivotally disposed on the first cutting set 23A, respectively comprise a blade portion B14, B15 and a edge portion B14', B15'. The edge portions B14', B15' of the fourth cutting member A4 and the fifth cutting member A5 are perpendicular to the blade portions B14, B15, respectively, and two sides of the edge portions B14', B15 respectively abut the first cutting member A1 and the second cutting member A2. In addition, the edge portion B14' of the fourth cutting member A4 and the edge portion B15' of the fifth cutting member A5 comprise the same of complementary shapes.

It should be noted that in the embodiment, the edge portions B14', B15' of the fourth cutting member A4 and the fifth cutting member A5 comprise linear shapes, but it is not limited thereto. As shown in FIG. 5, the edge portions B14', B15' of the fourth cutting member A4 and the fifth cutting member A5 may comprise complementary curved shapes or other shapes.

Figure 4A:
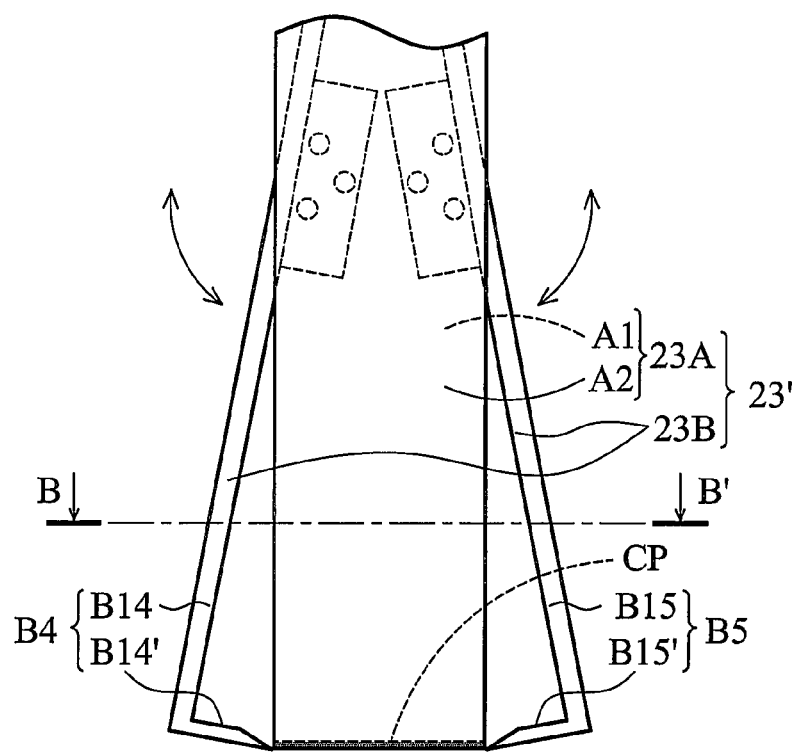
FIGS. 4A and 4B are schematic views of another embodiment of the selecting apparatus of the invention.
Figure 4B:
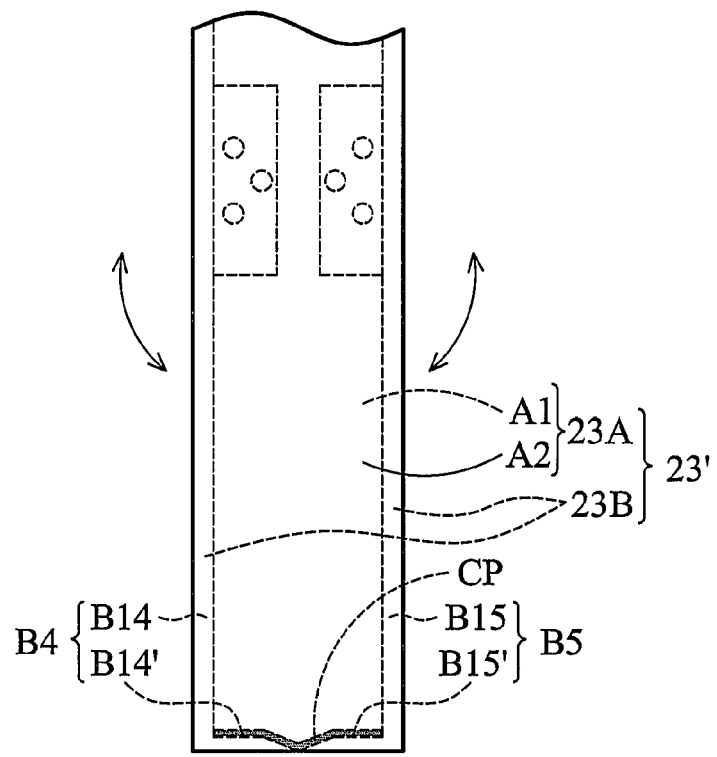
Figure 5A:
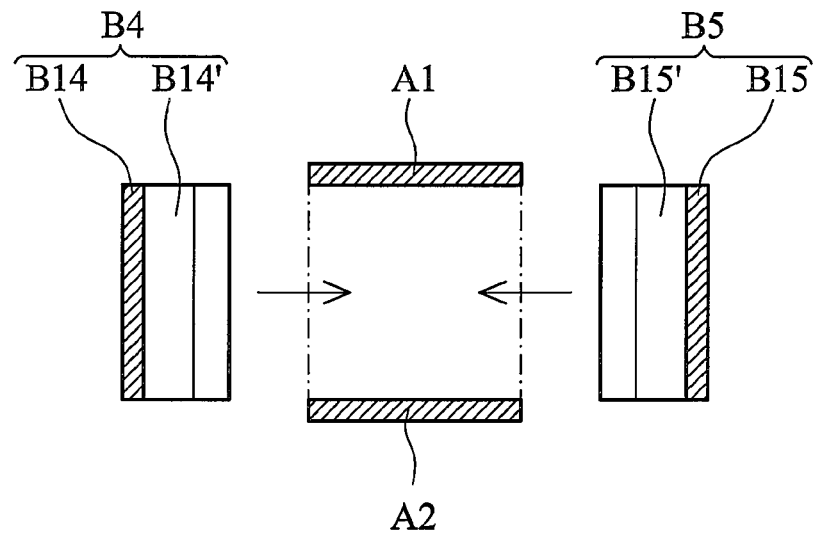
FIG. 5A is a sectional view along line B-B' in FIG. 4A.
Figure 5B:
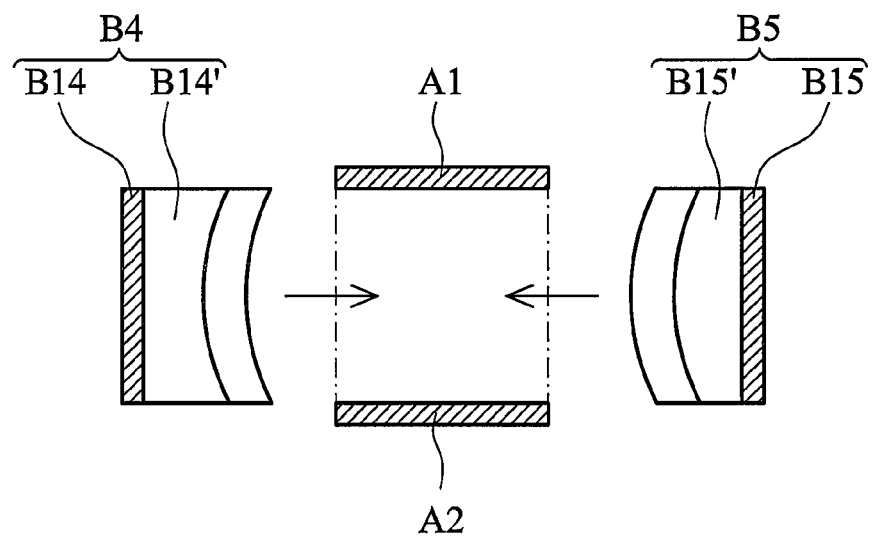
FIG. 5B is a sectional view of a variant embodiment of the dividing mechanism in FIG. 4A.

Referring to FIGS. 4A and 4B again, after the dividing mechanism 23' aligns with the portion CP of the cell/tissue mass C, the feeding mechanism 22 moves in the Y direction toward the cell/tissue mass C, allowing the first cutting set 23A to cut into the portion CP. Next, the fourth cutting member A4 and the fifth cutting member A5 of the second cutting set 23B rotates from the first position to the second position (as shown in FIG. 4B), allowing the edge portions B14', B15' thereof to cut into the cell/tissue mass C. The edge portions B14', B15 continuously move to shovel the portion CP of the cell/tissue mass C, such that the portion CP can be separated from the cell/tissue mass C and be limited between the first cutting set 23A and the second cutting set 23B. Furthermore, because the two sides of the edge portions B14', B15 respectively abut with the first cutting member A1 and the second cutting member A2, the portion CP of the cell/tissue mass C is completely shoveled by the second cutting set 23B during the rotation of the second cutting set 23B toward the first cutting set 23A (as shown in FIG. 4B).

In the described embodiments, the cell/tissue mass C is divided, cut and clamped by variant dividing mechanisms 23, 23'. After is portion CP of the cell/tissue mass C is clamped between the first cutting member 23A and the second cutting member 23B, the feeding mechanism 22 moves the dividing mechanism 23, 23' to a predetermined position, and usually the position is set to align with a carrier substrate. The second cutting set 23B moves from the second position to the first position in a direction opposite to the first cutting set 23A, allowing the portion CP of the cell/tissue mass C to separate from the first cutting set 23A and the second cutting set 23B. The portion CP of the cell/tissue mass C is then separated therefrom and dropped to the carrier substrate.

The invention provides the cell/tissue mass selecting apparatus with variant types of dividing mechanism. Each dividing mechanism comprises cutting tools that is adjustable according to different sizes of the selecting portion. The dividing mechanism accurately aligns with desired portion at any position, eliminating the pick up of unnecessary parts, such that every part of the cell/tissue mass is fully utilized. Compared with the cutting mechanism and transferring mechanism of the conventional cell/tissue mass selecting apparatus, the invention provides a single dividing mechanism to cut and move the cut cell/tissue mass, fully utilizing of selected area, minimizing the overall size of the selecting apparatus, increasing transferring rate and reducing probability of contamination of the cell/tissue mass.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A dividing mechanism for dividing cell/tissue mass, comprising:

a first cutting set, arranged to cut straight into the cell/tissues mass when moved in a first direction, comprising a first cutting member arranged to cut into the cell/tissue mass in a first plane and a second cutting member arranged to cut into the mass/tissue in a second plane parallel to the first plane when the cell/tissue mass is in a fixed position; and a second cutting set, connected with the first cutting set, rotatable in a direction in parallel with the first cutting member and the second cutting member, and arranged to cut into the cell/tissue mass in a third plane perpendicular to the first and the second planes when the cell/tissue mass is in the fixed position, wherein the second cutting set separates a portion from the cell/tissue mass in a second direction opposite to the first direction;

wherein two sides of the second cutting set abut the first cutting member and the second cutting member, respectively.

2. The dividing mechanism as claimed in claim 1, wherein the first cutting set further comprises a third cutting member, connected with the first cutting member and the second cutting member, and the second cutting set is disposed between the first cutting member and the second cutting member.

3. The dividing mechanism as claimed in claim 2, wherein the second cutting set comprises a blade portion and an edge portion perpendicular to the blade portion.

4. The dividing mechanism as claimed in claim 3, wherein the edge portion of the second cutting set and the third cutting member comprise the same or complementary shapes.

5. The dividing mechanism as claimed in claim 1, wherein the second cutting set further comprises a fourth cutting member and a fifth cutting member, two sides of the fourth cutting member and the fifth cutting member respectively abut the first cutting member and the second cutting member.

6. The dividing mechanism as claimed in claim 5, wherein the fourth cutting member and the fifth cutting member rotate toward each other.

7. The dividing mechanism as claimed in claim 5, wherein the fourth cutting member and the fifth cutting member respectively comprise a blade portion and a edge portion perpendicular to the blade portion.

8. The dividing mechanism as claimed in claim 5, wherein the edge portions of the fourth cutting member and the fifth cutting member comprise the same or complementary shapes.

9. The dividing mechanism as claimed in claim 1, wherein the second cutting set comprises a blade portion and an edge portion perpendicular to the blade portion.

\* \* \* \* \*